United States Patent
Manning et al.

(10) Patent No.: US 6,653,350 B1
(45) Date of Patent: Nov. 25, 2003

(54) METHODS OF TREATING OSTEOARTHRITIS WITH INDUCIBLE NITRIC OXIDE SYNTHASE INHIBITORS

(75) Inventors: Pamela T. Manning, Labadie, MO (US); Jane R. Connor, St. Louis, MO (US); Mark G. Currie, St. Charles, MO (US); Jean Pierre Pelletier, St. Lambert (CA); Johanne Martel Pelletier, St. Lambert (CA)

(73) Assignees: G.D. Searle & Co., Chicago, IL (US); Pharmacia Corporation

( * ) Notice: Subject to any disclaimer, the term of this patent is extended or adjusted under 35 U.S.C. 154(b) by 0 days.

(21) Appl. No.: 09/390,440

(22) Filed: Sep. 7, 1999

Related U.S. Application Data

(60) Provisional application No. 60/099,412, filed on Sep. 8, 1998.

(51) Int. Cl.$^7$ ................. A61K 31/195; A61K 31/13
(52) U.S. Cl. ................. 514/561; 514/638; 514/663
(58) Field of Search ................. 514/638, 561, 514/663

(56) References Cited

U.S. PATENT DOCUMENTS

| | | | |
|---|---|---|---|
| 5,246,970 A | 9/1993 | Williamson | 514/256 |
| 5,268,465 A | 12/1993 | Bredt | 435/252.3 |
| 5,449,688 A | 9/1995 | Wahl | 514/546 |
| 5,629,322 A | 5/1997 | Guthikonda | 514/313 |
| 5,684,008 A | 11/1997 | Hallinan | 514/256 |
| 5,759,836 A | 6/1998 | Amin | 435/189 |

FOREIGN PATENT DOCUMENTS

| | | |
|---|---|---|
| EP | 0 466 699 A1 | 1/1992 |
| WO | WO9313055 | 7/1993 |
| WO | WO 95/05811 | 3/1995 |
| WO | WO 95/13805 | 5/1995 |
| WO | WO 96/16648 | 6/1996 |
| WO | WO 96/30007 | 10/1996 |

OTHER PUBLICATIONS

Amin, A.R. et al. : <<A Novel Mechanism if Actuib of Tetracyclines : Effects on Nitric Oxide Synthases. Proceedings of the National Academy of Sciences of the United States of America (Nov. 26, 1996) 93 (24) 14014–9 XP000910849.

Murrell, A.C. et al. : <<Nitric oxide : An important articccular free radical.>> Journal of Bone and Joint Surgery (1996) 78(2) 265–274.

Pelletier, J.P et al.: <<Reduced progression of experimental osteoarthritis in vivo by selective inhibition of inducable nitric oxide synthase.>> Arthritis and Rheumatism (Jul. 1998) 41(7) 1275–1286.

Pelletier, J.P et al.: <<Selective inhibition of nitric oxide synthase reduces in vivo the progression of experimental osteoarthritic lesions and production of metalloproteases and interleukin–1>> Arthritis and Rheumatism (1997 Supp.) 40(9) S173.

Amin, A. R., et al., A novel mechanism of action of tetracyclines: Inhibitory effects on nitric oxide synthase activity in osteoarthritis, 1996, 60th National Scientific Meeting of the American College of Rheumatology and the 31st National Scientific Meeting of the Association of Rheumatology Health Professionals, Orlando, Florida, USA, Oct. 18–22, Arthritis & Rheumatism 39 (9 Suppl.):S211.

Amin, A. R., et al., Nonsteroidal antiinflammatory drugs inhibit the activity of COX–2 and nitric oxide synthase expressed in osteoarthritis–affected cartilage, 1996, 60th National Scientific Meeting of the American College of Rheumatology and the 31st National Scientific Meeting of the Association of Rheumatology Health Professionals, Orlando, Florida, USA, Oct. 18–22, Arthritis & Rheumatism 39 (9 Suppl.):S81.

Amin, A. R., et al., Osteoarthritis–affected cartilage spontaneously produces COX–2–derived prostaglandin E–2: Regulation by nitric oxide synthase, 1996, 60th National Scientific Meeting of the American College of Rheumatology and the 31st National Scientific Meeting of the Association of Rheumatology Health Professionals, Orlando, Florida, USA, Oct. 18–22. Arthritis & Rheumatism 39 (9 Suppl.):S272.

Amin, A. R., et al., The expression and regulation of nitric oxide synthase in human osteoarthritis–affected chondroycytes: evidence for up–regulated neuronal nitric oxide synthase, 1995, J. Exp. Med. 182:2097–2102.

Beckman, J. S. and Koppenol, W. H., Nitric oxide, superoxide, and peroxynitrite: the good, the bad, and the ugly, 1996, Am. J. Pathol. 271:C1424–C1437.

Beghetti, M. and Adatia, I., Recent developments in inhaled nitric oxide therapy, 1995, Exp. Opin. Invest. Drugs 4:985–995.

Bertolini, G. and Aquino, M., Nitric oxide synthase inhibitors: recent advances, 1994, Exp. Opin. Ther. Patents 4:1339–1345.

Blanco, F. J. et al., Chondrocyte apoptosis induced by nitric oxide, 1995, Am. J. Pathol. 146:75–85.

Cannon, G. W., et al., Suppression of adjuvant–induced arthritis in DA rats by incomplete Freund's adjuvant, 1993, Arthritis and Rheumatism 36:126–131.

(List continued on next page.)

Primary Examiner—Theodore J. Criares
(74) Attorney, Agent, or Firm—Philip B. Polster, II

(57) ABSTRACT

Methods of treating osteoarthritis by administering an therapeutically effective amount of NOS inhibitor are provided.

12 Claims, 2 Drawing Sheets

OTHER PUBLICATIONS

Cannon, G. W., et al., Nitric oxide production during adjuvant–induced and collagen–induced arthritis, 1996, Arthritis and Rheumatism (USA), 39:1677–1684.

Caron, J. P., et al., Chondroprotective effect of intraarticular injections of interleukin–1 receptor antagonist in experimental osteoarthritis: suppression of collagenase–1 expression, 1996, Arthritis and Rheumatism. 39:1535–1544.

Case J.P., Transin/stromelysin expression in rheumatoid synovium. A transformation–associated metalloproteinase secreted by phenotypically invasive synoviocytes, 1989, Am. J. Pathol. 135: 1055–1064.

Cawston, T. E. and Barrett, A. J., A rapid and reproducible assay for collagenase using [1–14C] acetylated collage, 1979, Anal. Biochem. 99:340–345.

Charles, I. G., et al., Cloning, characterization, and expression of a cDNA encoding an inducible nitric oxide synthase from the human chondroycyte, 1993, Proc. Natl. Acad. Sci. USU. 90:11419–11423.

Chavira, R. et al., Assaying proteinases with azocoll, 1984, Anal. Biochem, 136:446–450.

Clancy, R. M., et al., Alpha–5–beta–1 Integrin signaling in the chondrocyte: Nitric oxide disrupts fibronectin induced assembly of a subplasmalemmal acin–Rho A–FAK activation complex, 1996, 60th National Scientific Meeting of the American College of Rheumatology and the 31st National Scientific Meeting of the Association of Rheumatology Health Professionals, Orlando, Florida, USA, Oct. 18–22, Arthritis & Rheumatism 39 (9 Suppl.):S167.

Cochran F. R., et al., Insights into the role of nitric oxide in inflammatory arthritis, 1996, Medicinal Research Reviews, 16 (6), (Glaxo Wellcome Inc.).

Cochran F. R., Inhibition of nitric oxide synthesis as a therapeutic target for arthritis: recent reports, 1994, Exp. Opin. Invest. Drugs 3(5):529–531.

Connor, J. R., et al., Suppression of adjuvant–induced arthritis by selective inhibition of inducible nitric oxide synthase, 1995, Eur. J. Pharmacol. 273:15–24.

Conrozier, T., et al., Serum level of cartilage oligomeric matrix protein (comp) predicts the rate of disease progression in hip osteoarthritis (OA), 1996, 60th National Scientific Meeting of the American College of Rheumatology and the 31st National Scientific Meeting of the Association of Rheumatology Health Professionals, Orlando, Florida, USA, Oct. 18–22. Arthritis & Rheumatism 39 (9 Suppl.):S211.

Cook, H. T. & Cattell, V., Role of nitric oxide in immune–mediated diseases, 1996, Clinical Science (London), 91: 375–384.

Dore, S., et al., Human osteoarthritic chondrocytes posses an increased number of insulin–like growth factor 1 binding sites but are unresponsive to its stimulation, 1994, Possible role of IGF–1 binding Proteins. Arthritis and Rheumatism. 37:253–263.

Drapier, J. C., and Hibbs, J. B., Aconitases: A class of metalloproteins highly sensitive to nitric oxide synthesis, 1996, Methods in Enzymology. 269:26–36.

Eissa, N. T., et al., Alternative splicing of human inducible nitric–oxide synthase mRNA: Tissue–specific regulation and induction by cytokines, 1996, Journal of Biological Chemistry. 271: 43.

Evans, C. H., et al., Nitric oxide and cartilage metabolism, 1996, Methods in Enzymology. 269:75–88.

Evans, C. H., et al., Nitric oxide and its role in orthopaedic disease, 1995, Clin. Orthop. 312:275–294.

Farrell, A. J., et al., Increased concentrations of nitrite in synovial fluid and serum samples suggest increased nitric oxide synthesis in rheumatic diseases, 1992, Ann. Rheum. Dis. 51:1219–1222.

Fernandes, J. C., et al., Effects of tenidap on canine experimental osteoarthritis: I. Morphologic and metalloprotease analysis, 1995, Arthritis and Rheumatism. 38:1290–1303.

Frenkel, S. R., et al., Effects of nitric oxide on chondrocyte migration, adhesion, and cytoskeletal assembly, 1996, Arthritis & Rheumatism, 39:1905–1912.

Fuseler, J., Production of TNF, IL–6, and IL–1 Precedes enhanced nitric oxide production, bone erosion and pannus formation in development of acute experimental polyarthritis, 1996, 60th National Scientific Meeting of the American College of Rheumatology and the 31st National Scientific Meeting of the Association of Rheumatology Health Professionals, Orlando, Florida, USA, Oct. 18–22. Arthritis & Rheumatism 39(9Suppl.):S285.

Gilkeson, G., et al., Correlation of a serum measure of nitric oxide production with lupus disease activity measures, 1996, 60th National Scientific Meeting of the American College of Rheumatology and the 31st National Scientific Meeting of the Association of Rheumatology Health Professionals, Orlando, Florida, USA, Oct. 18–22. Arthritis & Rheumatism 39(9Suppl.):S251.

Grabowski P. S., Nitric oxide production in cells derived from the human joint, 1996, Br. J. Rheumatol. 35:207–212.

Hayem, G., et al., Lack of correlation between hydrogen peroxide production and nitric oxide production by cultured rabbit articular chondrocytes treated with fluoroquinolone antimicrobial agents, 1996, Toxicology In Vitro, 10 (5):551–555.

Hilliquin, P., et al., Detection of nitric oxide complexed in S–nitrosoproteins in rheumatoid arthritis (RA), 1996, 60th National Scientific Meeting of the American College of Rheumatology and the 31st National Scientific Meeting of the Association of Rheumatology Health Professionals, Orlando, Florida, USA, Oct. 18–22. Arthritis & Rheumatism 39(9Suppl.):S80.

Ialenti, A., et al., Modulation of Adjuvant Arthritis by Endogenous Nitric Oxide, 1996, British Journal of Pharmacology, 110(2):701–706.

Jang, D., et al., S–Substituted isothioureas are potent inhibitors of nitric oxide biosynthesis in cartilage, 1996, European Journal of Pharmacology. 312(3):341–347.

Jarvinen, T. A. H., et al., Nitric oxide mediates interleukin–1 induced inhibition of glycosaminoglycan synthesis in rat articular cartilage, 1995, Mediators of Inflammation, 4:107–111.

Jarvinen, T. A. H., et al., Endogenous nitric oxide and prostaglandin E–2 do not regulate the synthesis of each other in interleukin–1–beta–stimulated rat articular cartilage, 1996, Inflammation 20(6): 683–692.

Knowles, R. G., Nitric oxide synthases, 1996, 658th Meeting of the Biochemical Society, Biochemical Society Transactions, 24 (3): 875–878. (Glaxo Wellcome Medicines Res. Center).

Krier, J. D., et al., Nitric oxide and prostaglandin synthesis inhibition during volume expansion., 1996, 50th Annual Conference and Scientific Sessions of the Council for High Blood Pressure Research, Chicago, Illinois, USA, Sep. 17–20. Hypertension 28(3):521.

Kroncke, K. D., et al., Activated Macrophages Kill Pancreatic Syngeneic Islet Cells Via Arginine–Dependent Nitric Oxide Generation, 1991, Biochemical & Biophysical Research communication (USA), 175(3):752–8.

Lundberg, J. O. N., et al., Nitric oxide and inflammation: The answer is blowing in the wind, 1997, Nature Medicine (USA), 3(1): 30–31.

Mankin, H. J., et al., Biochemical and metabolic abnormalities in articular cartilage from osteo–arthritic human hips, 1971, The Journal of Bone and Joint Surgery. 53:523–537.

Mahowald., M. L., et al., Nitric oxide has opposite effects in acute vs. Chronic stages of antigen induced arthritis (AIA), 1996, 60th 60th National Scientific Meeting of the American College of Rheumatology and the 31st National Scientific Meeting of the Association of Rheumatology Health Professionals, Orlando, Florida, USA, Oct. 18–22. Arthritis & Rheumatism 39(9 Suppl.):S78.

McCartney–Francis, N., et al., Suppression of arthritis by an inhibitor of nitric oxide synthase, 1993, J. Exp. Med. 178:749–754.

McInnes, I. B. et al., Production of nitric oxide in the synovial membrane of rheumatoid and osteoarthritis patients, 1996, Journal of Experimental Medicine, 184 (4):1519–1524.

Moore, W. M., et al., L–N6–(1–Iminoethyl) lysine: A selective inhibitor of inducible nitric oxide synthase. 1994, J. Med. Chem. 37:3886–3888.

Morand, E. F., et al., Synovial macrophage lipocortin 1 involvement in dexamethasone inhibition of inducible nitric oxide synthase,1996, 60th National Scientific Meeting of the American College of Rheumatology and the 31st National Scientific Meeting of the Association of Rheumatology Health Professionals, Orlando, Florida, USA, Oct. 18–22. Arthritis & Rheumatism 39(9 Suppl.):S283.

Moulton P. J., Inflammatory joint disease: the role of cytokines, cyclooxygenases and reactive oxygen species, 1996, Br. J. Biomed. Sci. 53(4): 317–324.

Murrell, G. A. C., et al., Nitric oxide activates metalloprotease enzymes in articular cartilage, 1995, Biochem. Biophys. Res. Commun. 206:15–21.

Owens, M. W., et al., Inhibition of pleural mesothelial cell collagen synthesis by nitric oxide, 1996, Free Radical Biology and Medicine. 21(5):601–607.

Palmer R. M., et al., Induction of nitric oxide synthase in human chondroycytes. Biochem. Biophys. Res. Comm. 193:398–405.

Park S.–J., et al., Stem cell factor protects bone marrow–derived cultured mast cells (BMCMC) from cytocidal effect of nitric oxide secreted by fibroblasts in murine BMCMC–fibroblasts coculture, 1996, Biochemistry and Molecular Biology International 40(4): 721–729.

Parrott D. P., Synthesis of type I and type III collagen by synovial cells in tissue culture derived from patients with rheumatoid arthritis, osteoarthritis, and normal individuals, 1980, Pr oc. Soc. Exp. Biol. Med. 165(2), 335–344.

Pelletier, J. P., et al., The in vivo effects of intraarticular corticosteroid injections on cartilage lesions, stromelysin, interleukin–1 and oncogene protein synthesis in experimental osteoarthritis, 1995, Lab Invest. 72:578–586.

Pelletier, J. P., et al., Intraarticular injections with methylprednisolone acetate reduce osteoarthritis lesions in parallel with chondrocyte stromelysin synthesis in experimental osteoarthritis, 1994, Arthritis and Rheumatism 37:414–423.

Pichler R. H., et al., Differential expression of nitric oxide synthase (NOS) isoforms in CSA nephropathy: Potential regulation by osteopontin (OPN), 29th Annual Meeting of the American Society of Nephrology, New Orleans, Louisiana, USA, Nov. 3–6, 1996, Journal of the American Society of Nephrology 7(9):1763.

Renoux M., et al., Cellular activation products in osteoarthritis synovial fluid, 1995, Int. J. Clin. Pharmacol. Res. 15(4), 135–138.

Renoux M., et al., Release of mast cell mediators and nitrites into knee joint fluid in osteoarthritis—comparison with articular chondrocalcinosis and rheumatoid arthritis, 1996, Osteoarthritis Cartilage 4(3): 175–179.

Rollo, E. E., et al., Osteopontin inhibits nitric oxide production and cytotoxicity by activated RAW264.7 macrophages, 1996, Journal of Leukocyte Biology 60: 397–404.

Saklayen M. G. and Mandal, A. K., Nitric oxide: Biological and clinical perspectives, 1996, International Journal of Artificial Organs. 19:630–632.

Sakurai, H., et al., Nitric oxide production and inducible nitric oxide synthase expression in inflammatory arthritides, 1995, J. Clin. Invest. 96:2357–2363.

Tsukahara H., et al., Effect of nitric oxide synthase inhibitors on bone metabolism in growing rats, 1996, 29th Annual Meeting of the American Society of Nephrology, New Orleans, Louisiana, USA, Nov. 3–6, 1996. Journal of the American Society of Nephrology 7(9):1823.

Ueki Y., et al., Increased nitric oxide levels in patients with rheumatoid arthritis, 1996, J. Rheumatol. 23(2): 230–236.

Van Beuningen, H. M., et al., Transforming growth factor-–beta 1 stimulates chondrocyte proteoglycan synthesis and induces osteophyte formation in the murine knee joint, 1994, Lab Invest. 71:279–290.

Willis, W. D., et al., Nitric oxide release into the knee joint contributes to the development of heat hyperalgesia and inflammation in awake arthritic rats, 1996, Society for Neuroscience Abstracts 22: 1–3.

Zvaifler N., et al., Pannocytes: distinctive cells found in rheumatoid arthritis articular cartilage erosions, 1997, Am. J. Pathol. 150(3): 1125–1138.

Salvemini, D., et al., Nitric oxide: a key mediator in the early and late phase of carrageenan–induced rat paw inflammation, 1996, Br. J. Pharmacol. 118:829–838.

Salvemini, D., et al., Dual inhibition of nitric oxide and prostaglandin production contributes to the antiinflammatory properties of nitric oxide synthase inhibitors, 1995, J. Clin. Invest. 96:301–308.

Shabani, M., et al., Enhancement of wound repair with a topically applied nitric oxide–releasing polymer, 1996, Wound Repair and Regeneration 4(3): 353–362.

Stadler, J., et al., Articular chondrocytes synthesize nitric oxide in response to cytokines and lipopolysaccharide, 1991, J. Immunol. 147:3915–3920.

Stefanovic–Racic, M. K., et al., Nitric Oxide and Arthritis, 1993, Arthritis and Rheumatism. 36:1036–1044.

Stefanovic–Racic, M. K., et al., N–monomethyl arginine, an inhibitor of nitric oxide synthase, suppresses the development of adjuvant arthritisin rats, 1994, Arthritis and Rheumatism. 36:126–131.

Stefanovic–Racic, M. K. et al., Comaprison of the nitric oxide synthase inhibitors methylarginine and aminoguanidine as prophylactic and therapeuticc agents in rat adjuvant arthritis, 1995, J. Rheumatology. 22:1922–1928.

St. Clair, E. W., et al, Increased expression of nitric oxide synthase (NOS) type 2 by blood mononuclear cells (MNCs) in rheumatoid arthritis (RA), 1996, 60th National Scientific Meeting of the American College of Rheumatology and the 31st National Scientific Meeting of the Association of Rheumatology Health Professionals, Orlando, Florida, USA, Oct. 18–22. Arthritis & Rheumatism 39(9 Suppl.):S197.

St. Clair, E. W., et al., Increased expression of blood mononuclear cell nitric oxide synthase type 2 in rheumatoid arthritis patients, 1996, Journal of Experimental Medicine 184(3): 1173–1178.

Takahasi, T., et al., Elevated levels of nitric oxide in synovial fluid from patients with temporomandibular disorders, 1996, Oral Surgery Oral Medicine Oral Pathology Oral Radiology and Endodontics 82 (5): 505–509.

Taskiran, D., et al., Nitric Oxide mediates suppression of cartilage proteoglycan synthesis by interleukin–1, 1994, Biochem. Biophys. Res. Commun. 200:142–148.

METHODS OF TREATING OSTEOARTHRITIS WITH INDUCIBLE NITRIC OXIDE SYNTHASE INHIBITORS

CROSS-REFERENCE TO RELATED APPLICATION

This application claims priority from U.S. Provisional Application Ser. No. 60/099,412, filed Sep. 8, 1998.

FIELD OF INVENTION

This invention is generally related to nitric oxide synthase inhibitors and more specifically related to treating patients having osteoarthritis with nitric oxide synthase inhibitors.

BACKGROUND OF THE INVENTION

Nitric oxide (NO) is an inorganic reactive gas molecule, important in many physiological and pathological processes where it is synthesized by cells mediating vital biological functions.

Nitric oxide serves as a neurotransmitter in the brain, produced in small amounts on an intermittent basis in response to various endogenous molecular signals. Endothelial cells lining the blood vessels also produce nitric oxide in small amounts, relaxing smooth muscle and regulating blood pressure. Indeed, the production of nitric oxide has a significant effect on the function of circulating blood cells such as platelets and neutrophils as well as on smooth muscle including blood vessels and other organs. Nitric oxide is also synthesized in the immune systems. Endotoxin and cytokines induce the production of large amounts of nitric oxide in response to infectious and inflammatory stimuli, contributing to both host defense processes such as killing of bacteria and viruses as well as pathology associated with acute and chronic inflammation in a wide variety of diseases.

Nitric oxide is formed from L-arginine oxydation by at least three different isoforms of nitric oxide synthases (NOS) in mammalian cells divided into two distinct classes, constitutive and inducible. The three NOS isoforms have been identified as:

(i) Endothelial Nitric Oxide Synthase (eNOS); (Type III NOS), a constitutive, $Ca^{++}$/calmodulin dependent enzyme, located in the endothelium releasing nitric oxide in response to receptor or physical stimulation;
(ii) Neuronal Nitric Oxide Synthase (nNOS); (Type I NOS), a constitutive, $Ca^{++}$/calmodulin dependent enzyme, located in the brain releasing nitric oxide in response to receptor or physical stimulation; and
(iii) Inducible Nitric Oxide Sythase (iNOS); (Type II NOS), a $Ca^{++}$ independent enzyme which is induced after activation of vascular smooth muscle, macrophages, endothelial cells, and a number of other cells by endotoxin and cytokines. Once expressed, this inducible NOS synthesizes large amounts of nitric oxide (NO) for long periods.

Nitric oxide generated by the constitutive enzymes acts as a transduction mechanism underlying several physiological responses. For example, eNOS is critical for production of nitric oxide, originally identified as endothelium derived relaxation factor (ERDF). The nitric oxide generated by eNOS regulates blood pressure in animals, blood flow in man, and prevents leucocyte adhesion.

On the other hand, the nitric oxide produced in large amounts by the inducible enzyme in is a cytotoxic effector molecule. As disclosed in U.S. Pat. No. 5,629,322, incorporated herein by reference, iNOS has been cloned from human liver and identified in more than a dozen other cells and tissues including smooth muscle cells, the kidney, and numerous epithelial cells in a variety of tissues including the lung and colon. This enzyme is induced upon exposure to lipopolysaccharide (LPS) and cytokines such as gamma interferon (IFN-γ), interleukin-1β (IL-1β), and tumor necrosis factor (TNF). Once induced, nitric oxide production by iNOS continues over a prolonged period of time, and the activity of iNOS is relatively independent of intracellular Calcium concentrations.

iNOS is implicated in conditions leading to cytokine-induced hypotension including septic shock, hemodialysis and IL-2 therapy in cancer patients. The excess production of nitric oxide generated by the inducible form of nitric oxide synthase also appears to contribute to cytokine-mediated inflammation, cytotoxicity and tissue damage. accordingly, certain conditions have been identified where inhibiting nitric oxide production is advantageous. These conditions include arthritis, inflammatory bowel disease, cardivascular ischemia, diabetes, congestive heart failure, myocarditis, atherosclerosis, migraine, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (secondary to cardiac arrest), multiple sclerosis and other central nervous system disorders, for example Parkinson's disease and Alzheimer's disease, and other disorders mediated by NO including opiate tolerance in patients needing protracted opiate analgesics, and benzodiazepine tolerance in patients taking benzodiazepines, and other addictive behavior, for example, nicotine and eating disorders.

Further conditions in which there is an advantage in inhibiting NO production from L-arginine include systemic hypotension associated with septic and/or toxic shock induced by a wide variety of agents; therapy with cytokines such as TNF, IL-1 and IL-2; as an adjuvant to short term immunosuppression in transplant therapy; and as a chemopreventative.

Although the potential uses for NOS inhibitors has been implicated in numerous diseases, the efficacy and outcome of using a NOS inhibitor to prevent, treat and cure many diseases has never been identified. For example, U.S. Pat. No. 5,629,322 at Col. 15 beginning line 60 lists an enormity of disease types where the NOS inhibitors may be used to treat a disease. However, the disease types are named as a result of speculation, without examples or analysis. Examples of other compounds which inhibit the production of nitric oxide can be found in U.S. Pat. Nos. 5,684,008 and WO 93/13055, each incorporated by reference as if written herein.

The effect and efficacy of NOS inhibitors and specifically selective iNOS inhibitors in vivo on disease progression for the many diseases has not been addressed. Therefore, the outcome and consequence of the use of the inhibitors on disease progression in vivo in many cases remains unknown. Although some information has been generated in vivo in inflammatory arthritis, which models human rheumatoid arthritis, suggesting that either non-selective or in a few cases selective NOS inhibitors reduce disease severity, there are no reports of the use of NOS inhibitors to modulate experimental models of osteoarthritis. (18, 19, 21–24)

A need exists, therefore, to determine the effect NOS inhibitors have on the progression of osteoarthritis, and targeting new uses for NOS inhibitors and methods of treatment of osteoarthritis.

SUMMARY OF THE INVENTION

Accordingly, the present invention provides new methods of treating patients with osteoarthritis by modulating: 1) the amount of synovial fluid, 2) IL-1β levels; 3) the development of osteophytes; 4) the amount of cartilage degeneration; 5) metalloprotease production; and 6) acute joint injury through administering an effective amount of an iNOS inhibitor to the patient in need thereof. Specifically, the in vivo therapeutic efficacy of a selective inhibitor of the inducible NOS, N-iminoethyl-L-lysine (L-NIL), was used to determine the effect on the progression of lesions in osteoarthritis, on joint metalloprotease production and activity, and the levels of IL1β, prostaglandin $E_2$ ($PGE_2$) and nitrite/nitrate (the stable end products of nitric oxide) in synovial fluid.

Treatment with a selective inhibitor of iNOS reduced the severity of lesions, demonstrating the effectiveness of the inhibitor of iNOS in attenuating the progression of the disease. In addition, the inhibitor, L-NIL, reduced the production and the activity of metalloproteases in cartilage, degradative enzymes known to play a major role in the pathophysiology of osteoarthritic lesions. The effect was shown to be mediated, in part by the suppressive effect of the inhibitor on IL-1β production.

In addition, iNOS inhibitors attenuate the enhanced production of $PGE_2$ associated with an increased production of nitric oxide at sites of inflammation. Proinflammatory action of nitric oxide and $PGE_2$ are both suppressed by the selective iNOS inhibitor. Treatment in vivo with a selective iNOS inhibitor resulted in a marked decrease in the level of nitric oxide and $PGE_2$ in synovial fluid, and decreased the expression of iNOS and cyclooxygenase-2 (COX-2), the enzyme repsonsible for the generation of $PGE_2$.

This invention is the first to provide direct evidence that the in vivo suppression of nitric oxide production by selective inhibition of iNOS in osteoarthritic (OA) tissue is associated with a reduced in situ synthesis of interleukin-1 IL-1β by synovium, and metalloproteases by cartilage, as well as a reduced level of iNOS, peroxynitrite and COX-2, in OA tissue. This further elucidates the mechanisms responsible for the protective effect of the iNOS inhibitor on structural and biochemical changes seen in experimental osteoarthritis.

OA lesions in cartilage develop as a result of an imbalance in the anabolic and catabolic processes that occur during the development of the disease. (1) The excess production of nitric oxide generated by the inducible form of nitric oxide synthase contributes to cytokine-mediated inflammation, cytotoxicity and tissue damage. The present invention shows that the changes in the metabolism of chondrocytes in this disease are attributed, at least in part, to an increase in the synthesis of proinflammatory cytokines such as interluekin-1β (IFN-1β). This change in the function of the chondrocytes impacts the homeostasis of the cartilage matrix. (2)

Proinflammatory cytokines accelerate degradation of the cartilage matrix. (2,3) By inducing the synthesis of proteolytic enzymes, cytokines interfere with the action of growth factors such as the insulin growth factor-1 (IGF-1) binding proteins. (4) Moreover, the inflammatory cytokines also reduce the synthesis of aggrecan, one of the major matrix macromolecules responsible for the functional properties of articular cartilage. (5,6) An increased production of nitric oxide (NO) is one of the main factors by which IL-β reduces aggrecan synthesis. (5–7).

Nitric oxide is produced in large amounts by chondrocytes upon proinflammatory cytokine stimulation. (7–13) In contrast to normal cartilage, osteoarthritic cartilage spontaneously produces nitric oxide. (12–14) High levels of stable end product of nitric oxide have been found in the synovial fluid and serum of arthritic patients. (15) Similarly, the messenger RNA and protein for inducible NO synthase, an enzyme responsible for the generation of cytotoxic levels of NO, have also been detected in synovial tissue from OA patients. (14–16).

Until the present invention, nitric oxide was only believed to contribute to the development of arthritic lesions. (17–19) This hypothesis was based on in vitro data showing that nitric oxide enhances metalloprotease (MMP) activity and inhibits proteoglycan synthesis. (8,20) Furthermore, it has been hypothesized that nitric oxide reduced the synthesis of the IL-1 receptor antagonist in chondrocytes, a process possibly responsible for the enhanced effect of IL-1 on these cells. (13).

In the practice of the subject invention, seventeen dogs were used to test the effects of a NOS inhibitor in vivo on osteoarthritis. The OA dog model was created by sectioning the anterior cruciate ligament of the right stifle joint of twelve (12) dogs by a stab wound. Dogs were divided into three (3) groups. Group I had five (5) dogs (n=5) made up of unoperated dogs that received no treatment and considered normal. Group II consists of six (6) dogs having osteoarthritis (OA dogs) without treatment. Group III consists of six (6) OA dogs that received oral L-NIL (10 mg/kg) twice daily for ten (10) weeks beginning immediately after surgery.

The knees of the dogs treated with L-NIL showed a reduction in the incidence of osteophytes compared with the untreated dogs (58% vs. 92%) as well as in their size (1.92±0.58 mm vs. 5.08±0.66 mm). Macroscopically, L-NIL decreased the size of the cartilage lesions both on condyles and plateaus compared with the untreated dogs by about fifty percent (50%). At the histological level, the severity of cartilage lesions on the condyles and the severity of synovial inflammation were both statistically decreased in the L-NIL treated versus the untreated dogs. Treatment with L-NIL also significantly decreased both general MMP and stromelysin activity in the cartilage and the levels of IL-1β, $PGE_2$ and nitrite/nitrate in synovial fluid.

It is the object of the present invention to provide new methods of treating osteoarthritis by administrating a therapeutic effective amount of an iNOS inhibitor to a patient in need thereof.

Many other objects and purposes of the invention are clear from the following description of the invention.

While the specification concludes with claims particularly pointing out and specifically claiming the subject matter regarded as forming the present invention, it is believed that the invention will be better understood from the following detailed description of preferred embodiments.

DETAILED DESCRIPTION OF THE INVENTION

For the first time, a selective inhibitor of iNOS has been shown to reduce in vivo the progression of osteoarthritic lesions. In vivo treatment with a selective iNOS inhibitor also reduced the level of proinflammatory mediators, IL-1β and $PGE_2$ and nitrite/nitrate levels in the synovial fluid, and showed a marked reduction in metalloprotease activity and. expression in cartilage and the volume of joint effusion. It also resulted in a decreased expression of iNOS, peroxynitrite and COX-2 in the cartilage.

In earlier models, osteophyte formation was shown to be one of the predominant structural changes of osteoarthritis, particularly on the femoral condyles. (25–28) The formation and growth of osteophytes was hypothesized as being associated with inflamed synovium, mechanical factors, a variety of growth factors and cytokines. (33,34)

The subject invention teaches that treatment in vivo with a selective iNOS inhibitor reduces the growth of osteophytes and also decreases IL-1β production. Although in previous dog models, intraarticular injections of the IL-1 receptor antagonist was shown to decrease the formation of osteophytes, suggesting the role of IL-1β in the genesis of osteophytes, the effect of an iNOS inhibitor on osteophyte formation was unknown. (33)

The dog OA model used to test the methods of the subject invention has been previously used for testing the effects of anti-arthritic drugs in vivo. (25–28) This model is relevant to the human OA as it exhibits the development of progressive cartilage lesions. (32). In testing the method of the subject invention, cartilage lesions on both the condyles and plateaus of the untreated OA dogs at 10 weeks following surgery were significant in size and grade, as expected in this model and in accordance with our previous reports (25–28). Treatment with the selective iNOS inhibitor markedly reduced the size of cartilage lesions by more than 50%. L-NIL had an effect on the lesion grade, more specifically on the condyles, which was also reflected by the highly significant reduction in the histological severity of lesions. The protective effect of a selective NOS inhibitor was primarily attributable to the reduction in the severity of the structural changes (deepness of erosion) as indicated by the loss of safranin-O staining.

Our findings demonstrate selective iNOS inhibitors that mediate a reduction in the cartilage matrix breakdown. This could be due to a direct action of the iNOS inhibitor, as reflected by the reduction of the nitrite/nitrate level in synovial fluid, but is also likely secondary to the inhibition of proteolytic enzyme activity. Recent reports suggest that NO may stimulate MMP synthesis and/or activity in chondrocyte in vivo. (8,20) Our findings provide evidence that the in vivo cartilage MMP activity can be reduced by inhibiting iNOS activity and that the reduction in MMP activity in cartilage is associated with a decrease in the expression and synthesis of these proteases by chondrocytes. Therefore, the suppression of NO production by selective iNOS inhibitors preserved the cartilage proteoglycan content by reducing the level of MMP synthesis and activity in cartilage. Similarly, the decrease in severity of structural changes simultaneously with the inhibition of collagenase activity explains how selective iNOS inhibitors provide protection for the collagen network underlying the cartilage structure. Other possible mechanisms by which iNOS inhibition may ultimately result in a decrease in the destruction of the cartilage include a reduction in chondrocyte apoptotic cell death and a reduction in the formation of the toxic highly reactive oxidant, peroxynitrite.

The reduction in the degree of synovial inflammation in OA dogs treated with L-NIL compared to the synovium of untreated OA dogs is associated with a decrease in the level of IL-1β in the synovial membrane and fluid. The decrease in IL-1β synthesis mediated by L-NIL occurs either directly or by an indirect mechanisms. Nonetheless, this reduction in IL-1β contributes, at least in part, to the mechanism whereby the selective inhibitor reduces MPP synthesis in vivo.

In the treated dogs, the lower level of synovial inflammation was very striking, both macroscopically and microscopically, and was observed mainly as a very significant reduction of the villous hyperplasia and the number of infiltrating mononuclear cells in the tissue. This finding explains how treatment with a selective inhibitor reduces the amount of synovial fluid effusion.

Similar anti-inflammatory effects of NOS inhibitors were previously reported in carrageenan-stimulated air pouch and rat paw models of inflammation. The previous oral administration of L-NIL exerted other anti-inflammatory effects such as reducing the accumulation of nitrite/nitrate and the cellular infiltrate in the pouch fluid and the inflamed paw. In contrast, in vivo treatment of OA dogs with selective inhibitors reduced $PGE_2$ levels or PG isomerase activity as well as its expression. (37, 38)

Experimental Groups

Seventeen adult crossbred dogs (2–3 years), weighing 20 to 25 kg each, were used in this study. Surgical sectioning of the ACL of the right knee, through a stab wound, was performed on 12 dogs as previously described (25–28). Prior to surgery, animals were anesthetized intravenously with pentobarbital sodium (25 mg/kg) and incubated. Following surgery, the dogs were kept in animal care facilities for one week, then sent to a housing farm, where they were free to exercise in a large pen.

The dogs were randomly separated into three treatment groups: Group I (n=5) was made up of unoperated dogs that received no treatment (normal); Group II (n=6) were OA dogs that received no treatment; Group III (n=6) were OA dogs that were given 10 mg/kg L-NIL twice a day.

Drug Administration and Circulating Drug Level

L-NIL was administered twice daily at a dose of 10 mg/kg at 8 and 16 hours. The drug was given orally as a liquid solution. Drug treatment was initiated immediately after surgery for a duration of 10 weeks, after which time the animals were sacrificed. The concentration of L-NIL was measured in the serum mid-treatment and at the end of the study following 10 weeks of treatment, and in the synovial fluid at the end of the study only. L-NIL was measured using electrospray MS/MS (Sciex API III) in the multiple selection monitoring mode using the fragment ion (m/z 84) that originates from the compound.

Macroscopic Grading of Lesions

Immediately after sacrifice, the right knees of the dogs were dissected, placed on ice, and the synovial fluid aspirated and the volume measured. Each knee was examined for gross morphological changes, including the presence of osteophyte formation and cartilage lesions, as previously described (25–28). Examinations were performed by two independent, blinded observers. The degree of osteophyte formation was graded by measuring the maximal width (mm) of the spur on each femoral condyle. The cartilage changes on the medial and lateral femoral condyles and tibial plateaus were graded separately under a dissecting microscope (Stereozoom, Bausch & Lomb, Rochester, N.Y.).

The depth of erosion was graded on a scale of 0 to 4 as follows: 0=surface appears normal, 1=minimal fibrillation or a slight yellowish discoloration of the surface, 2=erosion extending into superficial or middle layers, 3=erosion extending into deep layers, 4=erosion extending to subchondral bone. The surface area of the articular surface changes was measured and expressed in $mm^2$.

Histological Grading

Histological evaluation was performed on sagittal sections of cartilage from the lesioned areas of each femoral condyle and tibial plateau as described (25–28). Specimens were dissected, fixed in 10% buffered formalin and embedded in paraffin for histological evaluation. Serial sections (5 $\mu$m) were stained with safranin-O. The severity of the OA lesions was graded on a scale of 0 to 14, by two independent observers, using the histological/histochemical scale of Mankin et al (29). This scale evaluates the severity of OA lesions based on the loss of staining with safranin-O (scale 0–4), cellular changes (scale 0–3), invasion of the tidemark by blood vessels (scale 0–1) and structural changes (scale 0–6). On this last scale, 0 indicates normal cartilage structure and 6 signifies erosion of the cartilage down to the subchondral bone. This scoring system was based on the most severe histological changes within each cartilage section.

Representative specimens of synovial membrane from the medial and lateral knee compartments were also dissected from underlying tissues. The specimens were fixed in 10% buffered formalin, embedded in paraffin, sectioned (5 $\mu$m) and stained with hematoxylin-eosin. Two synovial membrane specimens were examined for each compartment, with the highest score from each compartment retained. The average was calculated and considered as a unit for the whole knee. The severity of synovitis was graded on a scale of 0 to 10 (14) by two independent observers, adding the scores for 3 histologic criteria: synovial lining cell hyperplasia (scale 0–2), villous hyperplasia (scale 0–3), and degree of cellular infiltration by mononuclear and polymorphonuclear cells (scale 0–5).

Metalloprotease (MMP) Activity Assay

After macroscopic examination was performed and sections were taken for histological evaluation, the remaining cartilage from the femoral condyles, tibial plateaus and synovial membranes was carefully dissected.

Extraction of MMP was carried out as described (28). Briefly, the tissue was sliced and homogenized in the extraction buffer (50 mM Tris HCl, 10 mM $CaCl_2$, 2 M guanidine HCl, 0.05% Brij-35, pH 7.5). The mixture was stirred overnight at 4° C., and then centrifuged (18,000 g, 30 minutes, 4° C.). The supernatant was extensively dialyzed (48 hours at 4° C.) against an assay buffer (50 mM Tris HCl, 10 mM $CaCl_2$, 0.2M NaCl, 0.05% Brij-35, pH 7.5) using Spectrapor 4 dialysis tubing with a 12,000 Da cut-off (Spectrum Medical Industries, Los Angeles, Calif.).

The collagenase activity in tissue extract was measured using telopeptide-free type I collagen from rat tail tendon acetylated with $1^{14}$ Cl-acetic anhydride (30). One hundred microliters of $1^{14}$ Cl-collagen suspension (12,000 DPM) was incubated under the following conditions: 1) with an 100 $\mu$l aliquot of tissue extract, in the presence of 1 mM aminophenylmercuric acid (APMA), and 2) with an 100 $\mu$l aliquot of tissue extract, containing 1 mM APMA and 25 mM ethylenediaminetetraacetic acid (EDTA) serving as a blank. Each solution was incubated for 48 hours at 30° C., after which time each was centrifuged at 12,000 g for 15 minutes at 4° C. The radioactivity contained in the supernatant was determined using a beta scintillation counter (Beta Rack, Model 1218; LKB, Stockholm, Sweden). The total enzymatic activity was expressed in units per gram of tissue wet weight (w.w.), with one unit corresponding to the hydrolysis of 1 $\mu$g of substrate/hour at 30° C. Over 90% of the collagenase activity was inhibited by EDTA.

The general MMP activity in the cartilage extract was measured by the method of Chavira et al (31) using azocoll (Calbiochem-Novabiochem International, San Diego, Calif.) as the substrate. One hundred microliters of the azocoll suspension was incubated in a manner similar to the collagenase assay, but with 1 mM 1,10-phenanthroline serving as the blank. After incubation (48 hours at 37° C.), this solution was centrifuged (12,000 g for 15 minutes at 4° C.), and the supernatant's optical density determined by spectrophotometric analysis. The general MMP activity was expressed in units per gram of tissue w.w., in which one unit corresponded to the hydrolysis of 1 $\mu$g of substrate/hour at 37° C. The azocoll digesting activity in the extracts was inhibited by more than 90% by 1,10-phenanthroline.

Enzyme Immunoassay

The level of IL-1$\beta$ in the synovial fluid was determined using a specific solid phase, double antibody ELISA. $PGE_2$ was measured by an enzyme immunoassay. The IL-1$\beta$ kit was from BioSource International (Camarillo, Calif.), and the $PGE_2$ kit from Cayman Chemical Co. (Ann Arbor, Mich.). Sensitivity of the assay was 0.3 pa/ml for IL-1$\beta$ and 29 pg/ml for $PGE_2$. The measurements were performed in duplicate, and according to the manufacturer's specifications. The reaction was measured on a micro-ELISA Vmax photometer (Molecular Devices Corp., Menlo Park, Calif., USA). They were expressed as total pg or ng in the synovial fluid of the joint.

Nitric Oxide Assay

Nitrite and nitrate in synovial fluid were determined using a fluorometric assay as described (21). Briefly, synovial fluid was filtered through a 10,000 Da cut-off Ultrafree microcentrifuge filter unit (Millipore, Bedford, Mass.) at 14,000 rpm for 15 minutes. To convert nitrate to nitrite, 5–10 $\mu$l filtered synovial fluid was incubated in 20 mM Tris, pH 7.6 containing 40 μM NADPH and 14 mU of nitrate reductase in a final volume of 100 μl. After incubation for 5 minutes at 20° C., the fluorometric reaction was initiated by the addition of 10 μl of 0.05 mg/ml 2,3-diaminonaphthalene dissolved in 0.62M HCl. After 10 minutes at 20° C., the reaction was terminated with 10 μl 1.4 N NaOH. Fluorescence was measured at the wavelengths 365/450 nm (excitation/emission) using a fluorescence plate reader (IDEXX Laboratories, Westbrook, Me.). Nitrite was expressed as total nmol in the synovial fluid of the joint.

Immunohistochemical Studies

Cartilage specimens from condyles and plateaus, a well as synovial membrane, were processed immunohistochmical analysis as previously described. Briefly, specimens were fixed in 4% paraformaldehyde for 24 hours, then embedded in paraffin. Section (7 μm) of paraffin-embedded specimens were placed on Superfrost Plus slides (Fisher Scientific, Nepean, Ontario, Canada), deparaffinized in toluene, hydrated in a graded series of ethanol, and preincubated with chondroitinase ABC (0.25 units/ml) in phosphate buffered saline (PBS; Sigma Aldrich Canada Ltd., Oakville, Ontario, Canada) for 60 minutes at 37° C. Following this, the specimens were washed in PBS, then again in 0.3% hydrogen peroxide/methanol for 30 minutes. Slides were further incubated with 2% normal serum (Dimensions Laboratories, Mississauga, Ontario, Canada) for 20 minutes, blotted and then overlaid with: i) a rabbit polyclonal antibody (IgG) against iNOS (100 μg/ml, dilution 1/100, Santa Cruz Biotechnology Inc., Santa Cruz, Calif., USA) for 2 hours at room temperature in a humidified chamber; ii) a rabbit polyclonal (IgG) anti-nitrotyrosine antibody (dilution 1/100, Dr. P. Manning, Searle/Monsanto R&D, St. Louis, Mo., USA) for 1 hour at room temperature; iii) with a mouse monoclonal antibody (IgG) against rhIL-1β (1 mg/ml, dilution 1/25, BioSource International, Montreal, Quebec, Canada; iv) a rabbit polyclonal antibody (IgG) against rhstromelysin-1 (MMP-3; 500 μg/ml, dilution 1/1000, Oncogene Science, Cambridge, Mass., USA); v) a mouse monoclonal antibody against rhcollagenase (MMP-1; 100 μg/ml, dilution 1/500, Oncogene Science); or vi) a rabbit polyclonal antibody (IgG) against rhCOX-2 (dilution 1/500, Oxford Biomedical Research Inc., Oxford, Mich., USA). With the exception of the antibody against MMP-3, which was incubated for 18 hours at 4° C., all antibodies were incubated for 1 hour at room temperature.

Each slide was washed three times in PBS (pH 7.4) and stained using the avidin-biotin complex method (Vectastain ABCkit; Dimension Laboratories). This method entails incubation in the presence of the biotin-conjugated secondary antibody for 30 minutes at room temperature, followed by the addition of the avidin-biotin-peroxidase complex for 45 minutes. All incubations were carried out in a humified chamber, and the color developed with a 3,3'-diaminobenzidine (Dimension Laboratories) containing hydroxide peroxide.

To determine the specificity of staining, three control procedures were employed according to the same experimental protocol: 1) use of absorbed immune serum (1 hour, 37° C.) with a 10 to 20-fold molar excess of recombinant or purified antigen; 2) omission of the primary antibody; and 3) substitution of the primary antibody with an autologous preimmune serum. The purified antigens used in this study were rhIL-1β (Genzyme, Cambridge, Mass., USA), rhMMP-1, rhMMP-3, rhiNOS and rhCOX-2 (Monsanto/Searle, St. Louis, Mo., USA), and nitrotyrosine (Sigma-Aldrich, St. Louis, Mo., USA).

Several sections were made from each block of cartilage, and three slides from each specimen were processed for immunohistochemical analysis. Each section was examined under a light microscope (Leitz Orthoplan; Wild Leitz, Ville St-Laurent, Quebec, Canada), and photographed with Kodak Edtachrom 64 ASA film (Rochester, N.Y., USA).

Morphometric Analaysis

Cartilage

Cartilage samples from all medial and lateral femoral condyles and tibial plateaus were processed. From each cartilage specimen, three slides were processed for immunohistochemical studies. Quantification of the different antigens in cartilage and synovium was done using our previously published method with slight modifications. The level of protein synthesis was estimated by determining the number of chondrocytes staining positive within the different layers of cartilage. Each cartilage section was divided into six microscopic fields (×40; Leitz Diaplan), three fields at each of the following two zones: the superficial and upper intermediate layers, and the lower intermediate and deeper layers. The superficial layer includes chondrocytes of the immediate surface characterized by discoidal cells following the split-line pattern of the dominant fibrillar orientation, and the upper 50% of the transitional zone characterized by round or spheroidal cells. The deep layer includes cells of the lower 50% of the transitional zone and those aligned in columns. For each arthritic specimen, it was ensured prior to evaluation that an intact cartilage surface could be detected, and used as a marker for validation of morphometric analysis.

The total number of chondrocytes, and the number of chondrocytes staining positive for the specific antigen, were estimated for full-thickness cartilage. The final results were expressed as the percentage of chondrocytes staining positive for the antigen (cell score), with the maximum score being 100%. Each slide was subjected to double-blind evaluation, resulting in a variation of <5% between the scores. The data obtained from the medial lateral condyles and tibial plateaus were considered as independent for the purposes of statistical analysis.

Synovial Membrane

For synovial membrane analysis, a cell score of the different specimens was determined for each section using our previously published method. Each specimen was divided into 10 different areas: five microscopic fields (×40) at the synovial lining cell level, and five in the sublining area of the synovial membrane. The percentage of cells staining positive fore the specific antigen was evaluated in each field as described above for cartilage. The percentage of cells with positive staining was averaged for all five fields in each area of the synovium (synovial lining cells and mononuclear cell infiltrate). Each slide was evaluated blindly by two independent observers, resulting in a variation of <5% between the two scores. Cell count scores were given separately for the synovial lining cells and mononuclear cell infiltrate, with the maximum for each area being 100%.

Statistical Analysis

Mean values and standard errors of the mean were calculated. Statistical analysis was done using the Mann-Whitney U-test. P values less than 0.05 were considered significant.

Results

Circulating Drug Levels

The concentration of L-NIL was measured in the serum at mid-treatment and in the serum and synovial fluid following 10 weeks of treatment. Samples were obtained 2 h following drug administration. The mean concentration±SEM of L-NIL in the serum at mid-treatment and at the end of treatment was 201±33 and 119±24 $\mu$M, respectively. The concentration of L-NIL in the synovial fluid at the end of treatment was 96±18 $\mu$M, demonstrating access of the compound to the joint.

Macroscopic Findings

Osteophytes: In OA dogs, osteophytes were present in 92% of the condyles. Their mean±SEM width was 5.08±0.66. In dogs treated with L-NIL, osteophytes were present in only 58% of the condyles, and their size was smaller (1.92±0.58 mm; P<0.002) compared to the untreated OA dogs. Condyles from unoperated (normal) dogs were of normal appearance, and no osteophytes could be seen.

Cartilage: The cartilage on condyles and plateaus of normal dogs were macroscopically normal in appearance. In untreated OA dogs, cartilage lesions of moderate grade and size were present on both condyles and plateaus, with slightly more severe lesions on plateaus. Dogs treated with L-NIL presented a marked reduction in the severity of lesions on the condyles, with a decrease of approximately 50% in size and 20% in grade.

Synovial Membrane: Synovia from normal dogs had a white luster and were transparent in appearance. Synovia from OA dogs were hypertrophic and demonstrated a reddish-yellow discoloration and contained a large number of blood vessels. In OA dogs treated with L-NIL, the synovia were thinner and contained fewer blood vessels and the discoloration was less intense compared to untreated OA dogs.

Microscopic Findings

Cartilage: Cartilage from unoperated dogs had a normal histological appearance with the exception of a few dogs who showed either a minimal loss of safranin-O staining at the superficial layer or minimal irregularities of the cartilage surface. Specimens from untreated OA dogs had morphological changes including cartilage fibrillation and fissures, hypercellularity and cloning, and a loss of safranin-O staining. The histological score for the lesions on the condyles was similar to that on the plateaus. In the L-NIL-treated OA dogs, the lesions on the condyles were significantly less severe (P<0.005) compared to the untreated OA dogs. This difference was largely due to a decrease in severity of structural changes and loss of safranin-O staining. In accordance with macroscopic observation, no difference between the two OA groups (untreated and L-NIL-treated) was observed in the severity of histologic lesions on the plateaus.

Synovial Membrane: The histology of the synovia from the unoperated dogs was within normal limits, with the exception of a few specimens that had a minimal and focal villous hyperplasia (score=0.50±0.34). Synovia from the untreated OA dogs were thick, had numerous villosities, and showed synovial lining cell hyperplasia and moderate infiltration of mononuclear cells. The synovial inflammation in the OA dogs treated with L-NIL was less severe than the untreated OA dogs (score=2.50±0.18 vs 4.42±0.47; P<0.004). The reduction in the inflammation score following treatment with L-NIL resulted primarily from a reduction in the intensity of villous hyperplasia and mononuclear cell infiltration.

Metalloprotease Activity

General MMP Activity: The mean general MMP activity in cartilage and synovium was significantly higher (P<0.004 and P<0.02, respectively) in untreated OA dogs as compared to normal dogs. In the L-NIL-treated OA dogs, the enzyme activity was reduced in both cartilage and synovial membrane and a statistical difference reached for cartilage (P<0.004).

Collagenase: The mean activity of collagenase found in cartilage and synovium from OA dogs was significantly higher (P<0.002) compared to the activity found in normal dogs. The enzyme activity in both tissues was reduced by treatment with L-NIL, and again a statistical difference reached only for cartilage (P<0.004).

Values of IL-I$\beta$, Nitrite/Nitrate, and PGE$_2$ in Synovial Fluid

The volume of synovial fluid increased from 0.3±0.04 ml in normal dog joints to 6.8±1.0 ml in the joints of untreated OA dogs. Treatment with L-NIL reduced the volume by 68% to 2.4±0.8 ml (P<0.009). The total amount of IL-1$\beta$ in the synovial fluid of the normal dogs was very low (0.1 pg). A significantly higher level of IL-1$\beta$ (32.9±15.3 pg, P<0.001) was found in the untreated OA dogs. In OA dogs treated with L-NIL, the level of IL-1$\beta$ was significantly decreased to near normal amounts (0.5±0.2 pg) having a P<0.004 value when compared to the untreated OA. The total amount of nitrite/nitrate was also markedly increased in untreated OA synovial fluid (96.4±17.9 nmol, P<0.001), as compared to that in normal (6.5±0.8 nmol). The L-NIL-treated OA dogs exhibited a 53% decrease (48.6±12.9 nmol, P<0.04) in the total nitrite/nitrate content of synovial fluid over that of untreated OA dogs. Moreover, the total amount of PGE$_2$ was also reduced from 9.4±5.4 ng in untreated OA dog synovial fluid to 0.8±0.3 ng in L-NIL-treated OA dogs (P<0.009). Due to sample limitations, the amount of PGE$_2$ was not measured in normal dogs.

Synovial Membranes a) IL-1$\beta$

In unoperated dogs, IL-1$\beta$ was detected in only a very few cells in the synovial lining. In the untreated OA dogs, staining for IL-1$\beta$ was found in all specimens, and in both the synovial lining cells and the mononuclear cell infiltrate. The cell scores of OA synovial membrane specimens were significantly higher than those of unoperated dogs, both for mononuclear cell infiltrate and synovial lining cells.

In the L-NIL-treated dogs, although IL-1$\beta$ was expressed in all specimens, the cell score was significantly lower than in the untreated OA dogs, both for synovial lining cells (P<0.008) and mononuclear cell infiltrate (P<0.008). Controls using absorbed immune serum showed only background staining.

b) iNOS and 3-nitrotyrosine

With the exception of an occasional synovial lining cell, the synovial membrane of unoperated dogs showed no specific staining. In the OA synovial membrane of untreated dogs, a strong staining for both iNOS and 3-nitrotyrosine was observed in a small percentage of the lining and mononuclear infiltrating cells. The cell score for both lining and mononuclear cells was significantly higher when compared to unoperated dogs. There was a significant decrease in cell score for both lining and mononuclear cells, with the exception of the cell score for iNOS in mononuclear cells, in L-NIL-treated dogs. Controls using absorbed immune serum showed only background staining.

c) COX-2

In unoperated dogs, COX-2 staining was detected in only a few cells in the synovial lining. In the untreated dogs, there was a large number of cells, both in the synovial lining and the mononuclear cell infiltrate, that showed a positive staining for COX-2. Osteoarthritic dogs treated with L-NIL presented a marked decrease in the number of cells staining positive for COX-2, both in the lining and the mononuclear cell infiltrate.

Cartilage a) Metalloproteases

Only a few cells stained positive for collagenase-1 in the superficial and deep layers of condyles and plateaus in cartilage from unoperated dogs. The cell score was substantially higher in OA cartilage from operated untreated dogs, with a greater proportion of positive cells in the superficial layers. In contrast, operated dogs treated with L-NIL showed a marked and significant decrease in the collagenase-1 cell score in both condyles and plateaus.

Results for stromelysin-1 (General MMP) were similar to those for collagenase-1, with a marked and significant increase in cell score in OA cartilage from operated untreated dogs, with similar changes in both condyles and plateaus. Treatment with L-NIL significantly reduced stromelysin-1 cell score in both condyles and plateaus.

b) iNOS and 3-nitrotyrosine

Only in few cells in cartilage specimens from condyles and plateaus of unoperated dogs showed specific sytoplasmic staining for iNOS. These cells were located in both the superficial and the deep layers. There was a large and significant increase in number of chondrocytes expressing iNOS in OA cartilage, in both condyles and plateaus, that was significantly higher than specimens from unoperated dogs. The cell scores were similar in the superficial and deep layers. There was a very significantly decrease in the iNOS cell score in condyles and plateaus in the operated dogs treated with L-NIL.

The pattern for 3-nitrotyrosine staining was almost identical to that of iNOS. Only a few cells stained positive in all layers of cartilage from condyles and plateaus of unoperated dogs, while a marked and significant increase in cell score was found in OA cartilage. The number of positive chondrocytes was evenly distributed between the superficial and deep layers. Cartilage specimens from dogs treated with L-NIL showed a significantly lower cell score compared to that of untreated dogs, in both condyles and plateaus.

c) COX-2

The level of COX-2 was greatly increased in OA cartilage, whereas the number of chondrocytes staining positive for this enzyme was five-to-eight times greater than normal cartilage. OA dogs treated with L-NIL presented a very significant reduction in cell score on condyles and plateaus.

TABLE I

EXPRESSION OF IL-1β IN DOG SYNOVIAL TISSUE

| Groups | Synovial Lining (cell score) (p) ® | Mononuclear Cells (cell score) (p) |
|---|---|---|
| Unoperated* (n = 5) | 5.20 ± 0.65 (p < 0.008) | 0.23 ± 0.23 (p < 0.008) |
| OA§ (n = 5) | 58.71 ± 3.20 | 46.36 ± 4.76 |
| L-NIL@ (n = 5) | 33.32 ± 2.52 (p < 0.008) | 18.51 ± 2.84 (p < 0.008) |

Values are the mean ± SEM.
*Sacrificed animals neither operated nor treated.
§Operated animals sacrificed and tissue examined at 12 weeks after surgery.
@Operated animals sacrificed and tissue examined at 12 weeks after surgery; L-NIL given orally (10 mg/kg/qd/po) for 12 weeks beginning immediatly after surgery.
®Statistical analyses done by Mann-Whitney U-test; p values compared to OA group.

TABLE II

EXPRESSION OF iNOS AND 3-NITROTYROSINE IN DOG SYNOVIAL TISSUE

| | iNOS | | 3-Nitrotyrosine | |
|---|---|---|---|---|
| Groups | Synovial Lining (cell score) ® | Mononuclear Cells (cell score) | Synovial Lining (cell score) ® | Mononuclear Cells (cell score) |
| Unoperated* (n=5) | 0.002 ± 0.002 (p < 0.008) | 0.002 ± 0.002 (p < 0.06) | 1.36 ± 0.2 (p < 0.008) | 0.002 ± 0.002 (p < 0.008) |
| OA§ (n = 5) | 8.34 ± 0.96 | 5.26 ± 2.07 | 14.84 ± 3.57 | 8.87 ± 1.86 |

TABLE II-continued

EXPRESSION OF iNOS AND 3-NITROTYROSINE IN DOG SYNOVIAL TISSUE

| | iNOS | | 3-Nitrotyrosine | |
|---|---|---|---|---|
| Groups | Synovial Lining (cell score) ® | Mononuclear Cells (cell score) | Synovial Lining (cell score) ® | Mononuclear Cells (cell score) |
| L-NIL@ (n = 5) | 1.09 ± 0.39 ($p < 0.008$) | 2.46 ± 2.15 NS | 2.05 ± 0.3 ($p < 0.008$) | 2.36 ± 0.84 ($p < 0.02$) |

Values are the mean ± SEM.
*Sacrificed animals neither operated nor treated.
§Operated animals sacrificed and tissue examined at 12 weeks after surgery.
@Operated animals sacrificed and tissue examined at 12 weeks after surgery; L-NIL given orally (10 mg/kg/qd/po) for 12 weeks beginning immediately after surgery.
®Statistical analyses done by Mann-Whitney U-test; p values compared to OA group.

TABLE III

MACROSCOPIC GRADING OF FEMORAL CONDYLES AND TIBIAL PLATEAUS

| | | FEMORAL CONDYLES | | TIBIAL PLATEAUS | |
|---|---|---|---|---|---|
| GROUP | No. of Animals | Size ($mm^2$) | Grade (0–4 scale) | Size ($mm^2$) | Grade (0–4 scale) |
| Unoperated* | 5 | 0 | 0 | 0 | 0 |
| OA† | 6 | 15.33 ± 3.52 | 1.42 ± 0.19 | 17.02 ± 3.49 | 1.42 ± 0.29 |
| L-NIL§ | 6 | 7.33 ± 2.32 | 1.08 ± 0.26 | 9.75 ± 2.45 | 1.33 ± 0.26 |

Values are the mean ± SEM.
*Sacrificed animals were neither operated nor treated.
†Animals were sacrificed and tissue was examined 10 weeks after surgery.
§Animals were sacrificed and tissue was examined at 10 weeks after surgery. L-NIL (10 mg/kg twice daily) was given orally for 10 weeks, beginning after surgery.

TABLE IV

EXPRESSION OF COLLAGENASE (MMP-1) AND STROMELYSIN (MMP-3) IN DOG CARTILAGE

| | Collagenase-(MMP-1) | | Stromelysin-1 (MMP-3) | |
|---|---|---|---|---|
| Groups | Femoral Condyle (cell score) ® | Tibial Plateau (cell score) | Femoral Condyle (cell score) ® | Tibial Plateau (cell score) |
| Unoperated* (n = 5) | 4.12 ± 0.42 ($p < 0.001$) | 5.43 ± 0.71 ($p < 0.0001$) | 4.62 ± 0.61 ($p < 0.0001$) | 5.98 ± 0.52 ($p < 0.0001$) |
| OA§ (n = 5) | 30.28 ± 3.94 | 36.25 ± 3.58 | 43.48 ± 1.98 | 44.94 ± 2.17 |
| L-NIL@ (n = 5) | 10.02 ± 2.26 ($p < 0.0002$) | 18.25 ± 1.97 ($p < 0.0003$) | 34.45 ± 2.14 ($p < 0.006$) | 33.21 ± 1.90 ($p < 0.0001$) |

Values are the mean ± SEM.
*Sacrificed animals neither operated nor treated.
§Operated animals sacrificed and tissue examined at 12 weeks after surgery.
@Operated animals sacrificed and tissue examined at 12 weeks after surgery; L-NIL given orally (10 mg/kg/qd/po) for 12 weeks beginning immediately after surgery.
® Statistical analyses done by Mann-Whitney U-test; p values compared to OA group.

TABLE V

EXPRESSION OF INDUCIBLE NITRIC OXIDE SYNTHASE (iNOS) AND 3-NITROTYROSINE IN DOG CARTILAGE

| | Inducible Nitric Oxide Synthase (iNOS) | | 3-Nitrotyrosine | |
|---|---|---|---|---|
| Groups | Femoral Condyle (cell score) ® | Tibial Plateau (cell score) | Femoral Condyle (cell score) ® | Tibial Plateau (cell score) |
| Unoperated* (n = 5) | 5.49 ± 0.30 ($p < 0.0001$) | 6.98 ± 0.42 ($p < 0.0001$) | 5.36 ± 0.49 ($p < 0.0001$) | 6.27 ± 0.36 ($p < 0.0001$) |

TABLE V-continued

EXPRESSION OF INDUCIBLE NITRIC OXIDE SYNTHASE (iNOS) AND 3-NITROTYROSINE IN DOG CARTILAGE

| Groups | Inducible Nitric Oxide Synthase (iNOS) | | 3-Nitrotyrosine | |
|---|---|---|---|---|
| | Femoral Condyle (cell score) ⓡ | Tibial Plateau (cell score) | Femoral Condyle (cell score) ⓡ | Tibial Plateau (cell score) |
| OA§ (n = 5) | 47.11 ± 1.98 | 45.82 ± 2.13 | 36.68 ± 2.75 | 45.50 ± 2.35 |
| L-NIL@ (n = 5) | 26.46 ± 2.04 ($p < 0.0001$) | 35.82 ± 1.97 ($p < 0.001$) | 21.81 ± 2.14 ($p < 0.0004$) | 27.30 ± 1.88 ($p < 0.0001$) |

Values are the mean ± SEM.
*Sacrificed animals neither operated nor treated.
§Operated animals sacrificed and tissue examined at 12 weeks after surgery.
@Operated animals sacrificed and tissue examined at 12 weeks after surgery; L-NIL given orally (10 mg/kg/qd/po) for 12 weeks beginning immediately after surgery.
ⓡ Statistical analyses done by Mann-Whitney U-test; p values compared to OA group.

TABLE VI

COX-2 EXPRESSION IN DOG CARTILAGE

| Groups | Femoral Condyles (% of positive cells) (p) ⓡ | Tibial Plateaus (% of positive cells) (p) |
|---|---|---|
| Unoperated* (n = 5) | 5.02 ± 0.36 ($p < 0.0001$) | 7.64 ± 0.52 ($p < 0.0001$) |
| OA§ (n = 5) | 40.99 ± 3.26 | 39.74 ± 2.70 |
| L-NIL@ (n = 5) | 18.20 ± 2.29 ($p < 0.0001$) | 27.68 ± 2.12 ($p < 0.001$) |

Values are the mean ± SEM.
*Sacrificed animals neither operated nor treated.
§Operated animals sacrificed and tissue examined at 12 weeks after surgery.
@Operated animals sacrificed and tissue examined at 12 weeks after surgery; L-NIL given orally (10 mg/kg/qd/po) for 12 weeks beginning immediately after surgery.
ⓡ Statistical analyses done by Mann-Whitney U-test; p values compared to OA group.

The following references, patents and applications are hereby incorporated within this application as if written herein:

1. Pelletier, J. P., J. Martel-Pelletier, and D. S. Howell. 1997. Etiopathogenesis of osteoarthritis. In Arthritis and Allied Conditions. A Textbook of Rheumatology. W. J. Koopman, editor. Williams & Wilkins, Baltimore. 1969–1984.
2. Pelletier, J. P., J. A. DiBattista, P. J. Roughley, R. McCollum, and J. Martel-Pelletier. 1993. Cytokines and inflammation in cartilage degradation. In Osteoarthritis, Edition of Rheumatic Disease Clinics of North America. R. W. Moskowitz, editor. W. B. Saunders Company, Philadelphia. 545–568.
3. Dean, D. D. 1991. Proteinase-mediated cartilage degradation in osteoarthritis. [Review]. *Semin. Arthritis Rheum.* 20:2–11.
4. Dore, S., J. P.Pelletier, J. A. DiBattista, G. Tardif, P. Brazeau, and J. Martel-Pelletier. 1994. Human osteoarthritic chondrocytes possess an increased number of insulin-like growth factor 1 binding sites but are unresponsive to its stimulation. Possible role of IGF-1-Binding Proteins. *Arthritis Rheum.* 37:253–263.
5. Hickery, M. S., R. M. J.Palmer, I. G. Charles, S. Moncada, and M. T. Bayliss. 1994. The role of nitric oxide in IL-1 and TNFa-induced inhibition of proteoglycan synthesis in human articular cartilage. *Trans Orthop Res Soc* 19:77. (Abstr.)
6. Taskiran, D., M. Stefanovic-Racic, H. Georgescu, and C. Evans. 1994. Nitric oxide mediates suppression of cartilage proteoglycan synthesis by interleukin-1. *Biochem. Biophys. Res. Commun.* 200:142–148.
7. Jarvinen, T. A. H., T. Moilanen, T. L. N. Jarvinen, and E. Moilanen. 1995. Nitric oxide mediates interleukin-1 induced inhibition of glycosaminogylcan synthesis in rat articular cartilage. *Mediators of Inflammation* 4:107–111.
8. Stadler, J., M. Stefanovic-Racic, T. R. Billiar, R. D. Curran, L. A. McIntyre, H. I. Georgescu, R. L. Simmons, and C. H. Evans. 1991. Articular chondrocytes synthesize nitric oxide in response to cytokines and lipopolysaccharide. *J. Immunol.* 147:3915–3920.
9. Palmer, R. M. J., M. S. Hickery, I. G. Charles, S. Moncada, and M. T. Bayliss. 1993. Induction of nitric oxide synthase in human chondrocytes. *Biochem. Biophys. Res. Commun.* 193:398–405.
10. Maier, R., G. Bilbe, J. Rediske, and M. Lotz. 1994. Inducible nitric oxide synthase from human articular chondrocytes: cDNA cloning and analysis of mRNA expression. *Biochim. Biophys.Acta* 145:1208(Abstr.)
11, I. G. Charles, R. M. Palmer, M. S. Hickery, M. T. Bayliss, A. P. Chubb, V. S. Hall, D. W. Moss and S. Moncada. 1993. Cloning, characterization and expression of a cDNA encoding an inducible nitric oxide synthase from the human chondrocyte. *Proc. Natl. Acad. Sci. USA*. 90:11419–11423.
12. Amin, A. R., P. E. Di Cesare, P. Vyas, M. Attur, E. Tzeng, T. Billiar, S. Stuchin, and S. B. Abramson. 1995. The expression and regulation of nitric oxide synthase in human osteoarthritis-affected chondrocytes: evidence for an inducible "neuronal-like" nitric oxide synthase. *J. Exp. Med.* 182:2097–2102.
13. Pelletier, J. P., F. Mineau, P. Ranger, G. Tardif, and J. Martel-Pelletier. 1996. The increased synthesis of inducible nitric oxide inhibits IL-1Ra synthesis by human articular chondrocytes: possible role in osteoarthritic cartilage degradation. *Osteoarthritis Cartilage* 4:77–84.
14. I. B. McInnes, B. P. Leung, M. Field, X. Q. Wei, F. -P. Huang, R. D. Sturrock, A. Kinninmonth, J. Weidner, R. Mumford and F. Y. Liew. 1996. Production of nitric oxide in the synovial membrane of rheumatoid and osteoarthris patients. *J. Exp. Med.* 184:1519–1524.
15. Farrell, A. J., D. R. Blake, R. M. Palmer, and S. Moncada. 1992. Increased concentration of nitrite in synovial fluid and serum samples suggest increased nitric oxide synthesis in rheumatic diseases. *Ann Rheum. Dis.* 51:1219–1222.
16. Sakurai, H., H. Kohsaka, M. Liu, H. Higashiyama, Y. Hirata, K. Kanno, I. Saito, and N. Miyasaka. 1995. Nitric Oxide production and inducible nitric oxide synthase expression in inflammatory arthritides. *J. Clin. Invest.* 96:2357–2363.
17. Cannon, G. W., S. J. Openshaw, J. B. Hibbs, Jr., J. R. Hoidal, T. P. Huecksteadt, and M. M. Griffiths. 1996. Nitric oxide production during adjuvant-induced and collagen-induced arthritis. *Arthritis Rheum.* 39:1677–1684.
18. Evans, C. H., M. Stefanovic-Racic, and J. Lancaster. 1995. Nitric oxide and its role in orthopaedic disease. *Clin Orthop* 312:275–294.
19. Stefanovic-Racic, M., J. Stadler, and C. H. Evans. 1993. Nitric oxide and arthritis. *Arthritis Rheum.* 36:1036–1044.
20. Murrell, G. G. C., D. Jang, and R. J. Williams. 1995. Nitric oxide activates metalloprotease enzymes in articular cartilage. *Biochem Biophys Res Commun* 206:15–21.
21. Connor, J. R., P. T. Manning, S. L. Settle, W. M. Moore, G. M. Jerome, R. K. Webber, F. S. Tjoeng, and M. G. Currie. 1995. Suppression of adjuvant-induced arthritis by selective inhibition of inducible nitric oxide synthase. *Eur J Pharmacol* 273:15–24. 22. Stefanovic-Racic, M., K. Meyers, C. Meschter, J. W. Coffey, R. A. Hoffman, and C. H. Evans. 1994. N-monomethy arginine, an inhibitor of nitric oxide synthase, suppresses the development of adjuvant arthritis in rats. *Arthritis Rheum.* 37:1062–1069.
23. Stefanovic-Racic, M., K. Meyers, C. Meschter, J. W. Coffey, R. A. Hoffman, and C. H. Evans. 1995. Comparison of the nitric oxide synthase inhibitors methylarginine and aminoguanidine as prophylactic and therapeutic agents in rat adjuvant arthritis. *J. Rheumatol.* 22:1922–1928.
24. McCartney-Francis, N., J. B. Allen, D. E. Mizel, J. E. Albina, Q. Xie, D. F. Nathan, and S. M. Wahl. 1993. Suppression of arthritis by an inhibitor of nitric oxide synthase. *J. Exp. Med.* 178:749–754.
25. Moore, W. M., R. K. Webber, G. M. Jerome, F. S. Tjoeng, T. P. Misko, and M. G. Currie. 1994. L-N6-(1-Iminoethyl) lysine: a selective inhibitor of inducible nitric oxide synthase. *J Med Chem* 37:3886–3888.
26. Pelletier, J. P., J. A. DiBattista, J. P. Raynauld, S. Wilhelm, and J. Martel-Pelletier. 1995. The in vivo effects of intraarticular corticosteroid injections on cartilage lesions, stromelysin, iterleukin-1 and oncogene protein synthesis in experimental osteoarthritis. *Lab. Invest.* 72:578–586.
27. Pelletier, J. P., F. Mineau, J. P. Raynauld, J. F. Jr. Woessner, Z. Gunja-Smith, and J. Martel-Pelletier. 1994. Intraarticular injections with methylprednisolone acetate reduce osteoarthritic lesions in parallel with chondrocyte stromelysin synthesis in experimental osteoarthritis. *Arthritis Rheum.* 37:414–423.
28. Fernandes, J. C., J. Martel-Pelletier, I. G. Otterness, A. Lopez-Anaya, F. Mineau, G. Tardif, and J. P. Pelletier. 1995. Effects of tenidap on canine experimental osteoarthritis: I. Morphologic and metalloprotease analysis. *Arthritis Rheum.* 38:1290–1303.
29. Mankin, H. J., H. Dorfman, L. Lippiello, and A. Zarins. 1971. Biochemical and metabolic abnormalities in articular cartilage from ostreoarthritic human hips. II. Correlation of morphology with biochemical and metabolic data. *J. Bone Joint Surg. Am.* 53:523–537.
30. Cawson, T. E. and A. J. Barrett. 1979. A rapid and reproducible assay for collagenase using [1–14C] acetylated collagen. *Anal. Biochem.* 99:340–345.
31. Chavira, R. Jr., T. J. Burnett, and J. H. Hageman. 1984. Assaying proteinases with azocoll. *Anal. Biochem.* 136:446–450.
32. Brandt, K. D. 1994. Insights into the natural history of osteoarthritis provided by the cruciate-deficient dog. An animal model of osteoarthritis. [Review]. *Ann. NY Acad. Sci.* 732:199–205.
33. Caron, J. P., J. C. Fernandes, J. Martel-Pelletier, G. Tardif, F. Mineau, C. Geng, and J. P. Pelletier. 1996. Chondroprotective effect of intraarticular injections of interleukin-1 receptor antagonist in experimental osteoarthritis: suppression of collagenase-1 expression. *Arthritis Rheum.* 39:1535–1544.
34. Van Beuningen, H. M., P. M. Van der Kraan, O. J. Amtz, and W. B. van den Berg. 1994. Transforming growth factor-beta 1 stimulates articular chondrocyte proteoglycan synthesis and induces osteophyte formation in the murine knee joint. *Lab. Invest.* 71:279–290.
35. Blanco, F. J., R. L. Ochs, H. Schwarz and M. Lotz. 1995. Chondrocyte apoptosis induced by nitric oxide. *Am J. Pathol.* 146:75–85.
36. Beckman, J. S. and Koppenol. 1996. Nitric oxide, superoxide and peroxynitrite: the good, the bad, and the ugly. *Am. J. Physiol.* 271:C1424–C1437.
37. Salvemini, D., P. T. Manning, B. S. Zweifel, K. Siebert, J. Connor, M. G. Currie, P. Needleman, and J. L. Masferrer. 1995. Dual inhibition of nitric oxide and prostaglandin production contributes to the antiinflammatory properties of nitric oxide synthase inhibitors. *J. Clin. Invest.* 96:301–308.
38. Salvemini, D., Z. -Q. Wang, P. S. Wyatt, D. M. Bourdon, M. H. Marino, P. T. Manning, and M. G. Currie. 1996. Nitric oxide: a key mediator in the early and late phase of carrageenan-induced rat paw inflammation. *Br J Pharmacol* 118:829–838.

Figure 1B:
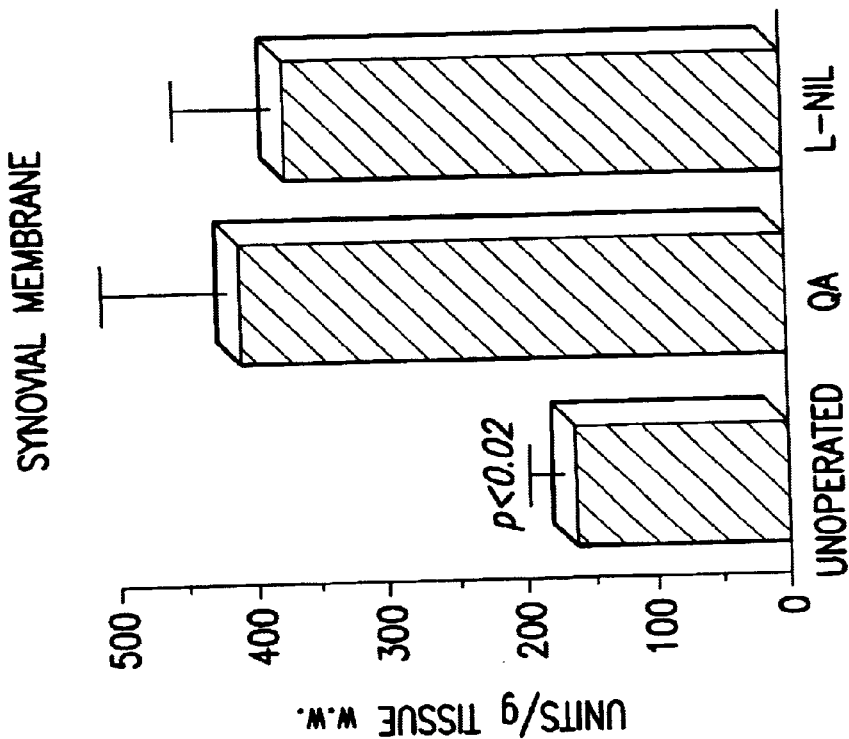
FIG. 1 Levels of general metalloprotease activity in articular cartilage and synovial membrane of dogs. Values are units/gms of tissue wet weight (w.w.). P values are versus the 10 week OA group, by Mann-Whitney U test.
Figure 1A:
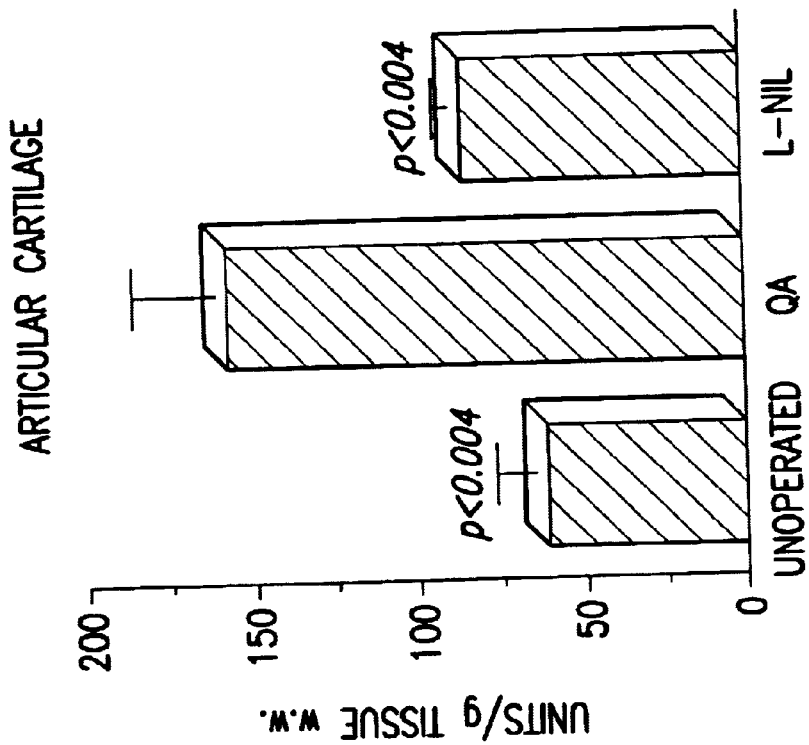
Figure 2B:
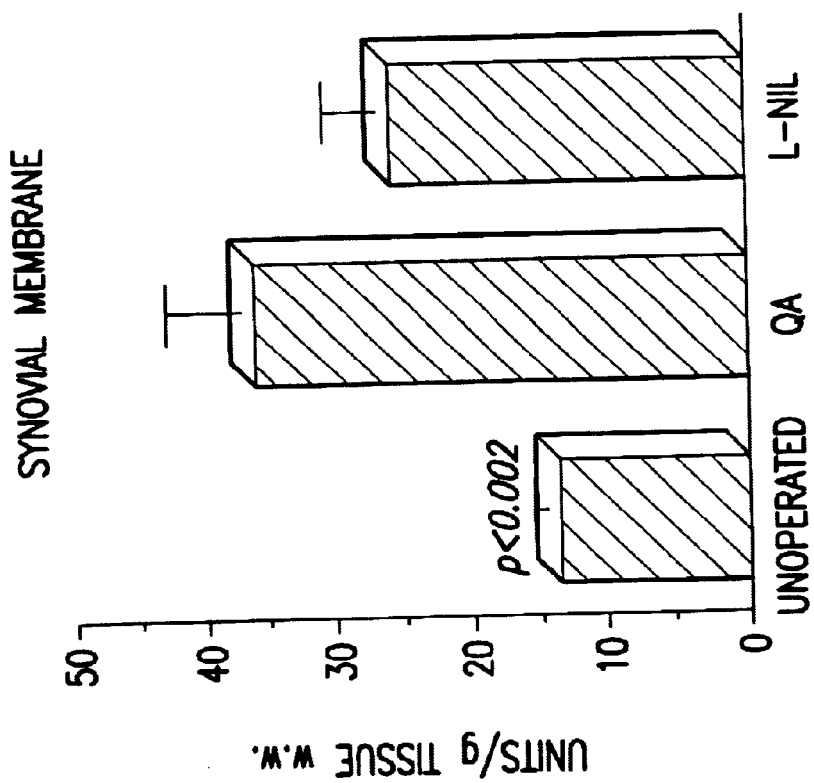
FIG. 2 Levels of collagenase activity in the cartilage and synovial membrane of dogs. Values are units/gms of tissue wet weight (w.w.). P values are versus the 10 week OA group, by Mann-Whitney U test.
Figure 2A:
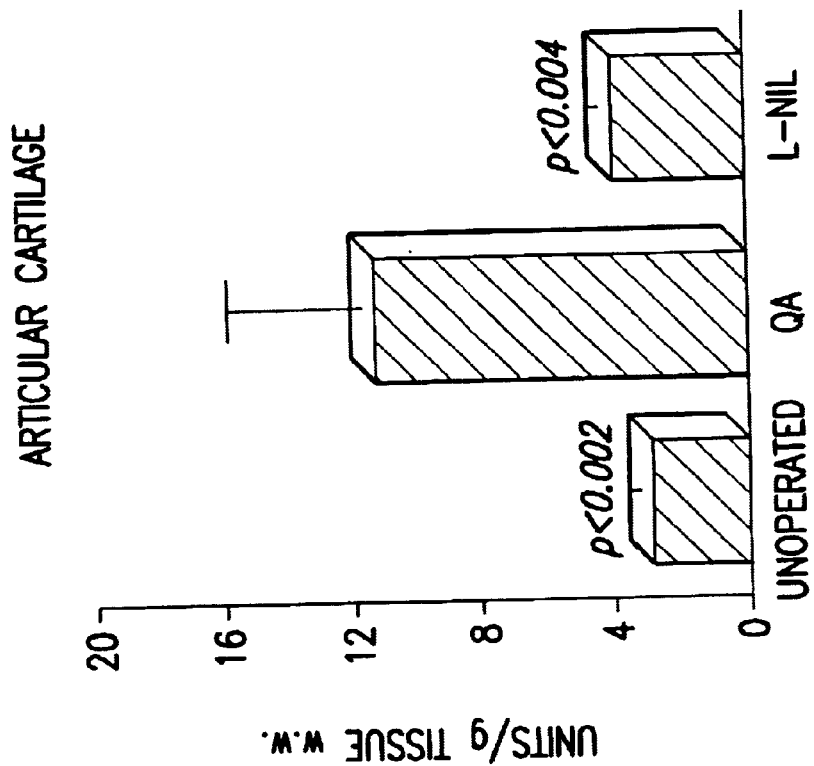

We claim:

1. A method of modulating IL-1β levels in a patient in need of such modulation comprising administering a therapeutic effective amount of N-iminoethyl-L-lysine to said patient.

2. A method of decreasing the amount of synovial fluid in a patient in need thereof by administering an effective amount of N-iminoethyl-L-lysine.

3. A method of treating osteoarthritis in a patient in need thereof comprising administering a therapeutic effective amount of N-iminoethyl-L-lysine, wherein the severity of said osteoarthritis is reduced.

4. The method of claim 3 wherein at least one lesion related to said osteoarthritis is reduced in size.

5. The method of claim 3 wherein the matrix disorganization of cartilage in said patient due to said osteoarthritis is modified.

6. A method of modulating osteophyte formation and development in a patient in need thereof comprising administering a therapeutic effective amount of N-iminoethyl-L-lysine.

7. A method of modulating cartilage lesions in a patient in need thereof by administering a therapeutic effective amount of N-iminoethyl-L-lysine.

8. The method of claim 7 wherein said lesions are on condyles.

9. The method of claim 7 wherein said lesions are on plateaus.

10. A method of preventing osteoarthritis in a patient in need thereof by administering an effective amount of N-iminoethyl-L-lysine.

11. A method of modulating metalloproteases in a patient by administering a therapeutic effective amount of N-iminoethyl-L-lysine to a patient in need thereof.

12. A method of treating acute joint injury by administering a therapeutic effective amount of N-iminoethyl-L-lysine to a patient in need thereof.

* * * * *